(12) United States Patent
Chang et al.

(10) Patent No.: US 12,364,399 B2
(45) Date of Patent: Jul. 22, 2025

(54) METHOD FOR MEASURING PHYSIOLOGICAL SIGNAL AND PHYSIOLOGICAL SIGNAL MEASUREMENT DEVICE

(71) Applicant: AU Optronics Corporation, Hsin-Chu (TW)

(72) Inventors: Shu-Hua Chang, Hsin-Chu (TW); Wei-Mei Chen, Hsin-Chu (TW); Chao-Hsiung Tseng, Hsin-Chu (TW); Ching-Huan Lin, Hsin-Chu (TW); Yi-Hsiang Lai, Hsin-Chu (TW); Chuang-Yueh Lin, Hsin-Chu (TW); Chun-I Wu, Hsin-Chu (TW); Yi-Chen Hsieh, Hsin-Chu (TW)

(73) Assignee: AU OPTRONICS CORPORATION, Hsin-Chu (TW)

( * ) Notice: Subject to any disclaimer, the term of this patent is extended or adjusted under 35 U.S.C. 154(b) by 420 days.

(21) Appl. No.: 17/844,241

(22) Filed: Jun. 20, 2022

(65) Prior Publication Data
US 2023/0117569 A1 Apr. 20, 2023

(30) Foreign Application Priority Data
Oct. 20, 2021 (CN) .......................... 202111221717.5

(51) Int. Cl.
*A61B 5/0205* (2006.01)
*A61B 5/00* (2006.01)
*A61B 5/05* (2021.01)

(52) U.S. Cl.
CPC .......... *A61B 5/0205* (2013.01); *A61B 5/0022* (2013.01); *A61B 5/05* (2013.01); *A61B 5/7203* (2013.01); *A61B 5/725* (2013.01); *A61B 5/7278* (2013.01); *A61B 5/743* (2013.01)

(58) Field of Classification Search
None
See application file for complete search history.

(56) References Cited

U.S. PATENT DOCUMENTS

| 2019/0094350 | A1 | 3/2019 | Baheti et al. |
| 2019/0190767 | A1* | 6/2019 | Kim .................... H04L 27/3863 |
| 2020/0196866 | A1 | 6/2020 | Chiou |
| 2020/0313680 | A1* | 10/2020 | Tseng .................... A61B 5/7225 |
| 2021/0208286 | A1* | 7/2021 | Turpin ...................... G01S 3/74 |
| 2021/0398666 | A1* | 12/2021 | Maslik ................. A61B 5/4842 |

FOREIGN PATENT DOCUMENTS

| CN | 103110422 A | 5/2013 |
| CN | 106264501 A | 1/2017 |
| CN | 106297194 A | 1/2017 |
| CN | 108272447 A | 7/2018 |
| CN | 109557535 A | 4/2019 |
| CN | 113257415 A | 8/2021 |
| CN | 113261925 A | 8/2021 |

* cited by examiner

*Primary Examiner* — Whitney Moore
(74) *Attorney, Agent, or Firm* — WPAT, PC (57) ABSTRACT

A method for measuring a physiological signal includes following steps: detecting a first physiological signal of a target; receiving the first physiological signal to generate a first signal and a second signal by a radar sensor; selecting one of the first signal and the second signal to generate a plurality of original signals, which a phase difference is formed between the first signal and the second signal; and capturing a respiration signal and a heartbeat signal according to the plurality of original signals.

19 Claims, 8 Drawing Sheets

METHOD FOR MEASURING PHYSIOLOGICAL SIGNAL AND PHYSIOLOGICAL SIGNAL MEASUREMENT DEVICE

RELATED APPLICATIONS

This application claims priority to China Application Serial Number 202111221717.5, filed on Oct. 20, 2021, which is herein incorporated by reference in its entirety.

BACKGROUND

Field of Invention

The present disclosure relates to an electronic device and a method.

More particularly, the present disclosure relates to a physiological signal measurement device and a method for measuring a physiological signal.

Description of Related Art

Conventional techniques for monitoring physiological signals of human bodies are divided into electrocardiography (ECG) signal measured by touch devices and light volume change signals measured by cameras using a red or green light. Since touch devices need to touch human bodies, it may make a subject feel uncomfortable.

In addition, due to a use of a red or green light cameras for sensing, light volume change signals is easily affected by a light source. At a same time, cameras sometimes capture the subject's face information, resulting in privacy issues.

For the foregoing reason, there is a need to provide other suitable designs for measuring a physiological signal to solve the problems of the prior art.

SUMMARY

One aspect of the present disclosure provides a method for measuring a physiological signal. The method for measuring a physiological signal includes following steps: detecting a first physiological signal of a target; receiving the first physiological signal to generate a first signal and a second signal by a radar sensor; selecting one of the first signal and the second signal to generate a plurality of original signals, which a phase difference is formed between the first signal and the second signal; and capturing a respiration signal and a heartbeat signal according to the plurality of original signals.

Another aspect of the present disclosure provides a physiological signal measurement device. The physiological signal measurement device includes a radar sensor and a processor. The radar sensor is configured to emit a sensing signal so as to detect a physiological signal of a target. The radar sensor is configured to generate a first signal and a second signal according to the physiological signal. The processor is coupled to the radar sensor. The processor is configured to selecting one of the first signal and the second signal to generate a plurality of original signals. A phase difference is formed between the first signal and the second signal. The processor is configured to capture a respiration signal and a heartbeat signal according to the plurality of original signals.

BRIEF DESCRIPTION OF THE DRAWINGS

The present disclosure can be more fully understood by reading the following detailed description of the embodiment, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

The terminology used herein is for the purpose of describing particular example embodiments only and is not intended to be limiting of the present disclosure. As used herein, the singular forms "a," "an" and "the" are intended to include the plural forms as well, unless the context clearly indicates otherwise.

Furthermore, it should be understood that the terms, "comprising", "including", "having", "containing", "involving" and the like, used herein are open-ended, that is, including but not limited to.

The terms used in this specification and claims, unless otherwise stated, generally have their ordinary meanings in the art, within the context of the disclosure, and in the specific context where each term is used. Certain terms that are used to describe the disclosure are discussed below, or elsewhere in the specification, to provide additional guidance to the practitioner skilled in the art regarding the description of the disclosure.

Figure 1:
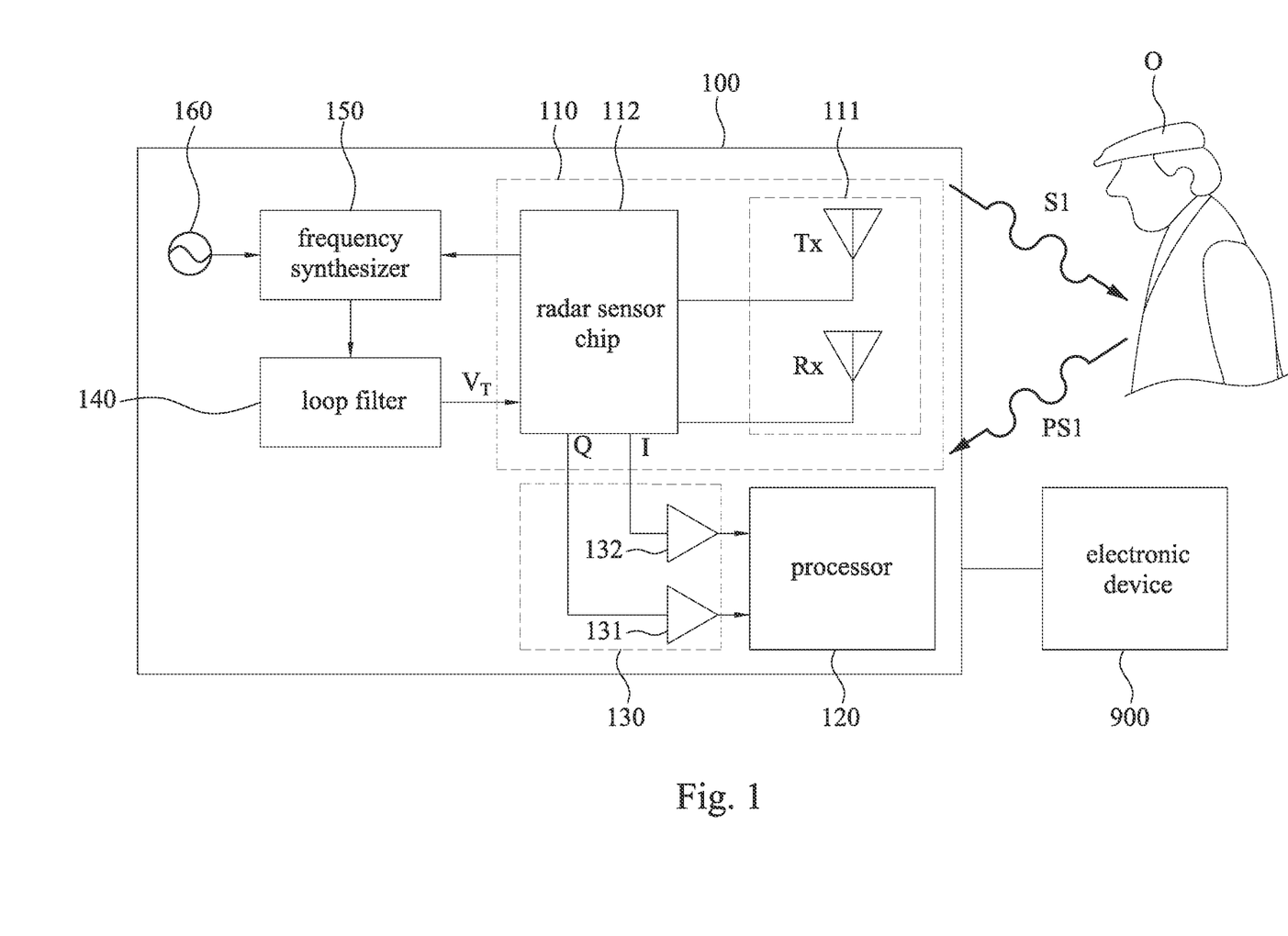
FIG. 1 depicts a schematic diagram of a physiological signal measurement device according to some embodiments of the present disclosure.

FIG. 1 depicts a schematic diagram of a physiological signal measurement device 100 according to some embodiments of the present disclosure. In some embodiments, the physiological signal measurement device 100 includes a radar sensor 110, a processor 120, an amplifier circuit 130, a loop filter 140, a frequency synthesizer 150, and a reference signal source 160.

In some embodiments, the radar sensor 110 is coupled to the amplifier circuit 130, the loop filter 140, and the frequency synthesizer 150. In some embodiments, the processor 120 is coupled to the amplifier circuit 130. In some embodiments, the frequency synthesizer 150 is coupled to the loop filter 140 and the reference signal source 160.

In some embodiments, the radar sensor 110 is configured to emit a sensing signal S1 to detect and receive a physiological signal PS1 of a target O. The radar sensor 110 is configured to generate a first signal I and a second signal Q according to the physiological signal PS1. The processor 120 is configured to select one of the first signal I and the second signal Q to generate a plurality of original signals. A phase difference is formed between the first signal I and the second signal Q. The processor 120 is configured to generate a heartbeat signal and a respiration signal of the target O according to the plurality of original signals. In some embodiments, the target O includes people and experimental animals. In some embodiments, the target O is mainly in a stationary state when the target O is measured by the physiological signal measuring device 100 of the present disclosure.

In some embodiments, the radar sensor 110 includes a millimeter wave radar. In some embodiments, a frequency of the sensing signal S1 emitted by the radar sensor 110 is about 2.4 GHZ.

In some embodiments, the radar sensor 110 includes a wireless high frequency circuit 111 and a radar sensor chip 112. The wireless high frequency circuit 111 includes a radar RF (radio frequency) transmitter antenna Tx (Transmit) and a receiving antenna Rx (Receive) used to capture reflected electromagnetic waves. In some embodiments, the radar RF transmitter antenna Tx is configured to emit the sensing signal S1. The receiving antenna Rx is configured to receive the physiological signal PS1. The physiological signal PS1 is a reflected electromagnetic wave signal that the sensing signal S1 is transmitted to a chest position of the target O (e.g. the position close to the heart) so as to generate. In some embodiments, the wireless high frequency circuit 111 includes a plurality of beam-steerable liquid crystal antenna components. Each of the plurality of beam-steerable liquid crystal antenna components is configured to emit the sensing signal S1 and receive the physiological signal PS1. In some embodiments, the radar sensor chip 112 is configured to control the radar RF transmitter antenna Tx to emit the sensing signal S1. The radar sensor chip 112 is configured to divide the received physiological signal PS1 into the first signal I and the second signal Q. The radar sensor 110 of the present disclosure mainly uses the plurality of beam-steerable liquid crystal antenna components, and operations of the plurality of beam-steerable liquid crystal antenna components will be described in following paragraphs.

In some embodiments, a distance from the sensing signal S1 emitted by radar sensor 110 to target O is between 0.1 m to 8 m. An emission range of a horizontal angle of the sensing signal S1 is about 150 degrees.

In some embodiments, the processor 120 includes but is not limited to a single processor and the integration of multiple microprocessors, such as central processing units (CPU), graphic processing units (GPU), and microcontroller units (MCU). The processor 120 is a microcomputer that integrates central processing units, memories, timers/counters, and a plurality of electronic components for input and output interfaces on an integrated circuit chip. In some embodiments, the processor 120 is further configured to output the heartbeat signal and the respiration signal to an electronic device 900. The electronic device 900 includes a display panel. The display panel is configured to a graphical user interface (GUI). In some embodiments, the electronic device 900 includes one of mobile phones, computers, notebook computers and wearable devices.

In some embodiments, an amplifier circuit 130 includes a first amplifier 131 and a second amplifier 132. Each of the first amplifier 131 and the second amplifier 132 includes a baseband amplifier. In some embodiments, the amplifier circuit 130 is configured to transmit the first signal I and the second signal Q of the radar sensor 110, and is configured to increase a plurality of output powers of the first signal and the second signal. In some embodiments, the second amplifier 132 is configured to transmit the first signal I, and is configured to increase an output power of the first signal I. In some embodiments, the first amplifier 131 is configured to transmit the second signal Q, and is configured to increase an output power of the second signal Q. It should be noted that the first signal I and the second signal Q are signals for different data channels. A phase difference is formed between the first signal I and the second signal Q.

In some embodiments, the loop filter 140 is configured to determine a bandwidth of an internal circuit of the physiological signal measurement device 100 (not shown in figure) and is configured to convert a reference signal of the reference signal source 160 to a control voltage. The loop filter 140 is further configured to remove a disturbed high frequency signal in the physiological signal PS1.

In some embodiments, the frequency synthesizer 150 is configured to generate a plurality of discrete frequency signals according to a reference signal or a plurality of reference signals.

In some embodiments, the reference signal source 160 is configured to provide the reference signal or the plurality of reference signals to the frequency synthesizer 150.

In some embodiments, a combination of the loop filter 140, the frequency synthesizer 150, and the reference signal source 160 is a phase locked loop.

The combination of the loop filter 140, the frequency synthesizer 150, and the reference signal source 160 is configured to demodulate signals (e.g. physiological signal PS1), recover the plurality of original signals from high-noise communication channels (e.g. physiological signal PS1), generate frequencies that are integer multiples of an input signal frequency, or generate an accurate clock pulse signal in a digital circuit.

Figure 2:
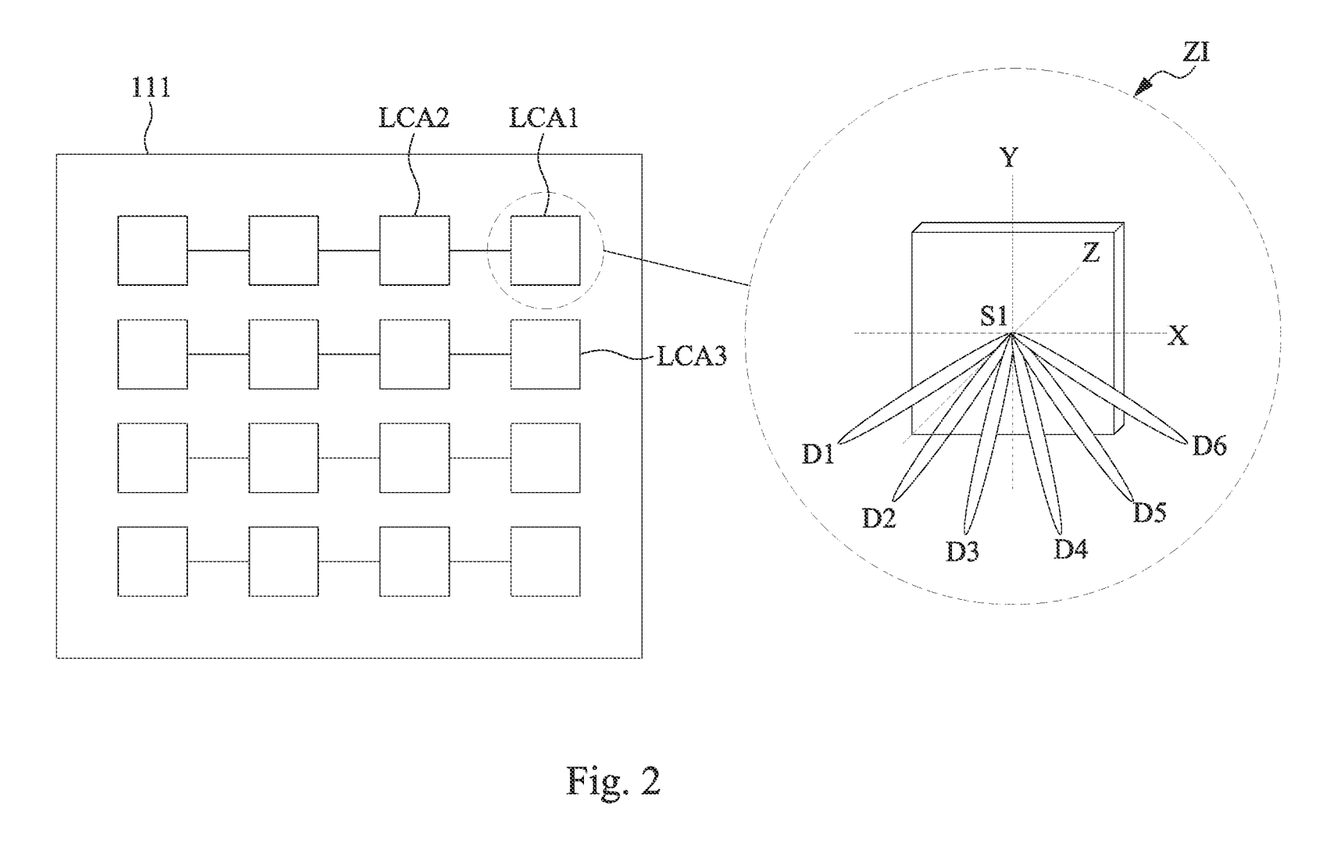
FIG. 2 depicts a schematic diagram of beam-steerable liquid crystal antenna components of a physiological signal measurement device according to some embodiments of the present disclosure.

FIG. 2 depicts a schematic diagram of beam-steerable liquid crystal antenna components of a physiological signal measurement device 100 according to some embodiments of the present disclosure. In some embodiments, please refer to FIG. 1 and FIG. 2, FIG. 2 shows the physiological signal measurement device 100 shown in FIG. 1 using beam-steerable liquid crystal antenna components.

In some embodiments, the wireless high frequency circuit 111 includes beam-steerable liquid crystal antenna components (e. g.: a beam-steerable liquid crystal antenna component LCA1, a beam-steerable liquid crystal antenna component LCA2, and a beam-steerable liquid crystal antenna component LCA3). Each of the beam-steerable liquid crystal antenna components is configured to emit the sensing signal S1 so as to receive the physiological signal PS1. In some embodiments, the plurality of the beam-steerable liquid crystal antenna components are arranged as an array shown in FIG. 2. In some embodiments, locations of the plurality of the beam-steerable liquid crystal antenna components can be designed according to actual need, and not limited to embodiments shown in the figure. In some embodiments, the beam-steerable liquid crystal antenna component LCA1 and beam-steerable liquid crystal antenna component LCA2 are antennas in the same row and are coupled to each other as shown in the figure. The beam-steerable liquid crystal antenna component LCA1 and the beam-steerable liquid crystal antenna component LCA3 are antennas in the same column, and are not coupled to each other as shown in the figure. It should be noted that beam directions of sensing signals emitted by antennas in different rows can be the same or different.

In some embodiments, please refer to FIG. 1 and FIG. 2, an enlarged view ZI on a right side of FIG. 2 is an enlarged view of the beam-steerable liquid crystal antenna element LCA1 in three-dimensional space. The beam-steerable liquid crystal antenna element LCA1 is configured to emit the sensing signal S1 along a first beam direction D1. The beam-steerable liquid crystal antenna element LCA1 is configured to change a beam direction of the sensing signal S1 into a second beam direction D2, a third beam direction D3, a fourth beam direction D4, a fifth beam direction D5 or a sixth beam direction D6 according to a control signal of the radar sensor 110. The first beam direction D1, the second beam direction D2, the third beam direction D3, the fourth beam direction D4, the fifth beam direction D5, and the sixth beam direction D6 are not parallel to each other in three-dimensional space. It should be note that a radiation direction is manipulated by changing a phase of a signal fed into the beam-steerable liquid crystal antenna elements, without changing positions of the beam-steerable liquid crystal antenna elements. It should be note that directions of coordinate axes of a three-dimensional space are the X-axis, the Y-axis and the Z-axis respectively.

Figure 3:
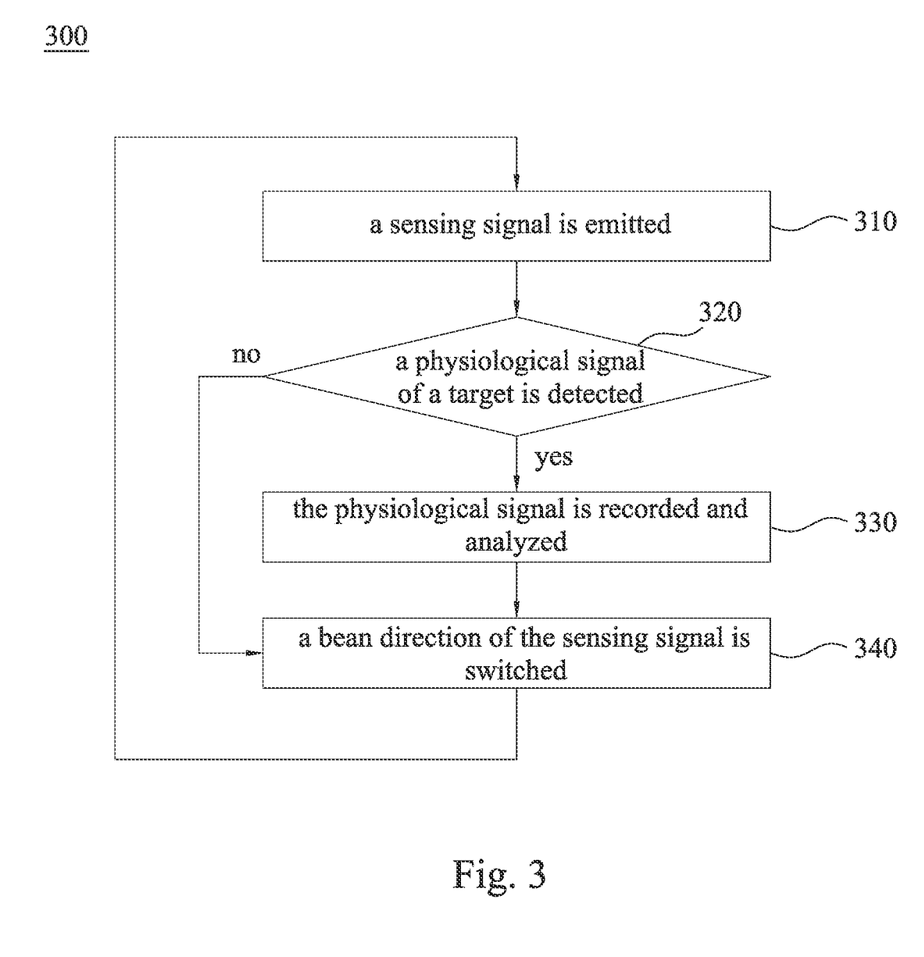
FIG. 3 depicts a flow chart of a method for measuring a physiological signal according to some embodiments of the present disclosure.

In some embodiments, in order to facilitate the understanding the method 300 for measuring the physiological signal, please refer to FIG. 1 to FIG. 3. FIG. 3 depicts a flow chart of a method 300 for measuring a physiological signal according to some embodiments of the present disclosure. In some embodiments, the method 300 for measuring the physiological signal can be executed by the physiological signal measurement device 100 of the present disclosure.

In step 310, a sensing signal is emitted. In some embodiments, please refer to FIG. 1 to FIG. 3, a sensing signal S1 is emitted by the radar sensor 110 of the physiological signal measurement device 100.

In step 320, a physiological signal of a target is detected. In some embodiments, please refer to FIG. 1 to FIG. 3, after a physiological signal PS1 is received by the radar sensor 110 of the physiological signal measurement device 100, the physiological signal measurement device 100 is configured to execute a step 330. In some embodiments, the radar sensor 110 is configured to determine whether the physiological signal PS1 of a target O is sensed. If the radar sensor 110 does not detect the physiological signal PS1 of the target O, the step 340 is executed.

In some embodiments, if a number of a target is two or more, the physiological signal measurement device 100 is configured to adjust a beam direction of the sensing signal S1 until the radar sensor 110 of the physiological signal measurement device 100 receives the physiological signal PS1. After the physiological signal measurement device 100 is configured to receive and record a physiological signal of a first target (not shown in the figure), the physiological signal measurement device 100 is configured to adjust a beam direction of the sensing signal S1 to sense a physiological signal of a next target (not shown in the figure). In some embodiments, a measurement time for receiving and recording a physiological signal of each target (not shown in the figure)) is about 20 seconds, but the measurement time is not limited to embodiments of the present disclosure.

In step 330, the physiological signal is recorded and analyzed. In some embodiments, following the aforementioned step 320, the radar sensor 110 is configured to detect the physiological signal PS1 of the target O. The radar sensor 110 is configured to generate the first signal I and the second signal Q of different data channels according to the physiological signal PS1, and the physiological signal PS1 is recorded and analyzed by the processor 120. Detailed steps for the processor 120 to record and analyze the physiological signal PS1 will be described in following paragraphs.

In step 340, a bean direction of the sensing signal is switched. In some embodiments, please refer to FIG. 1 to FIG. 3, the radar sensor 110 is configured to output a control signal to adjust the first beam direction D1 of the sensing signal S1 of the beam-steerable liquid crystal antenna components (e.g.: a beam-steerable liquid crystal antenna component LCA1, a beam-steerable liquid crystal antenna component LCA2, and a beam-steerable liquid crystal antenna component LCA3) of the radar sensor 110 as one of second beam direction D2 to the sixth beam direction D6.

Figure 4:
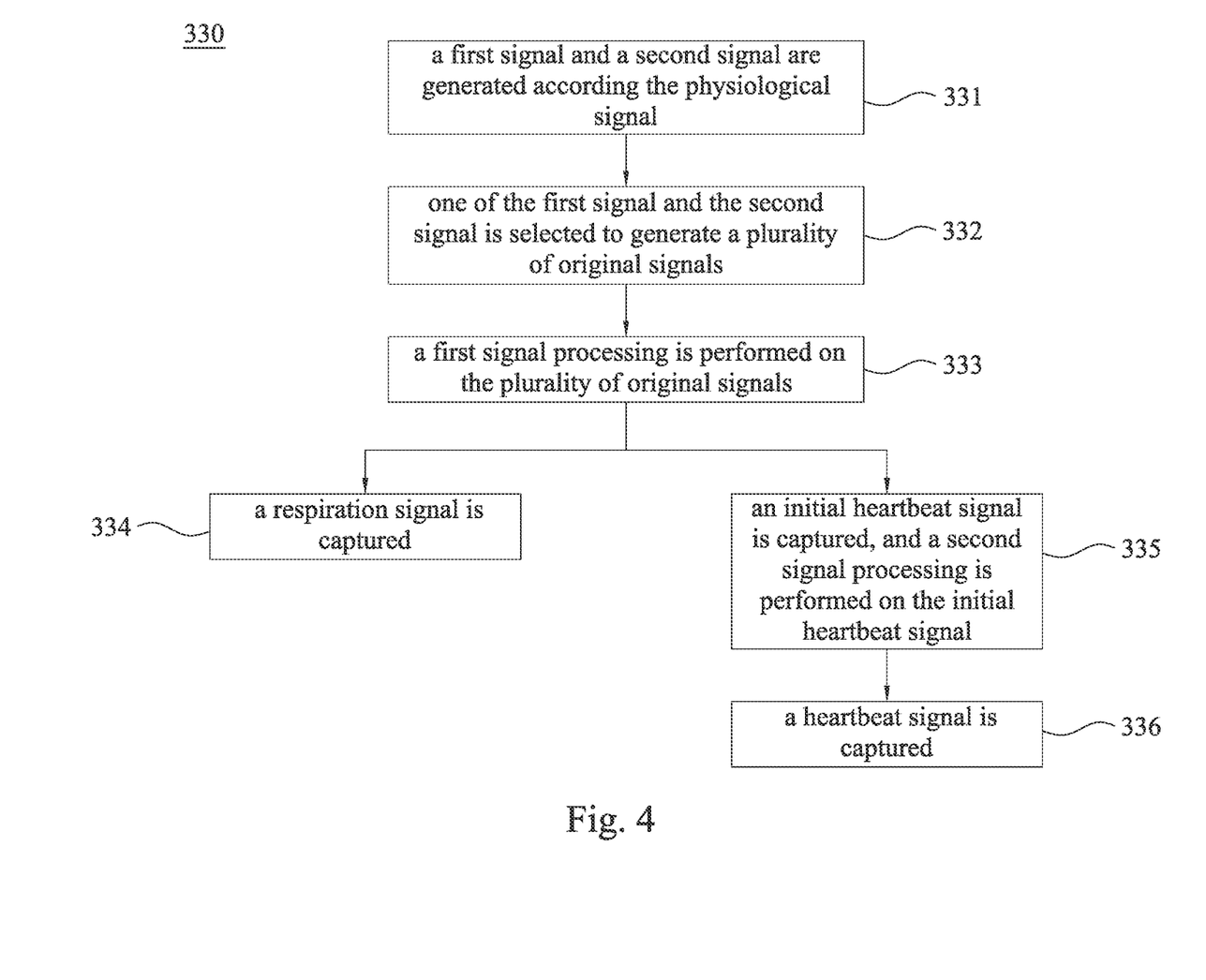
FIG. 4 depicts a flow chart of a method for measuring a physiological signal according to some embodiments of the present disclosure.
Figure 5:
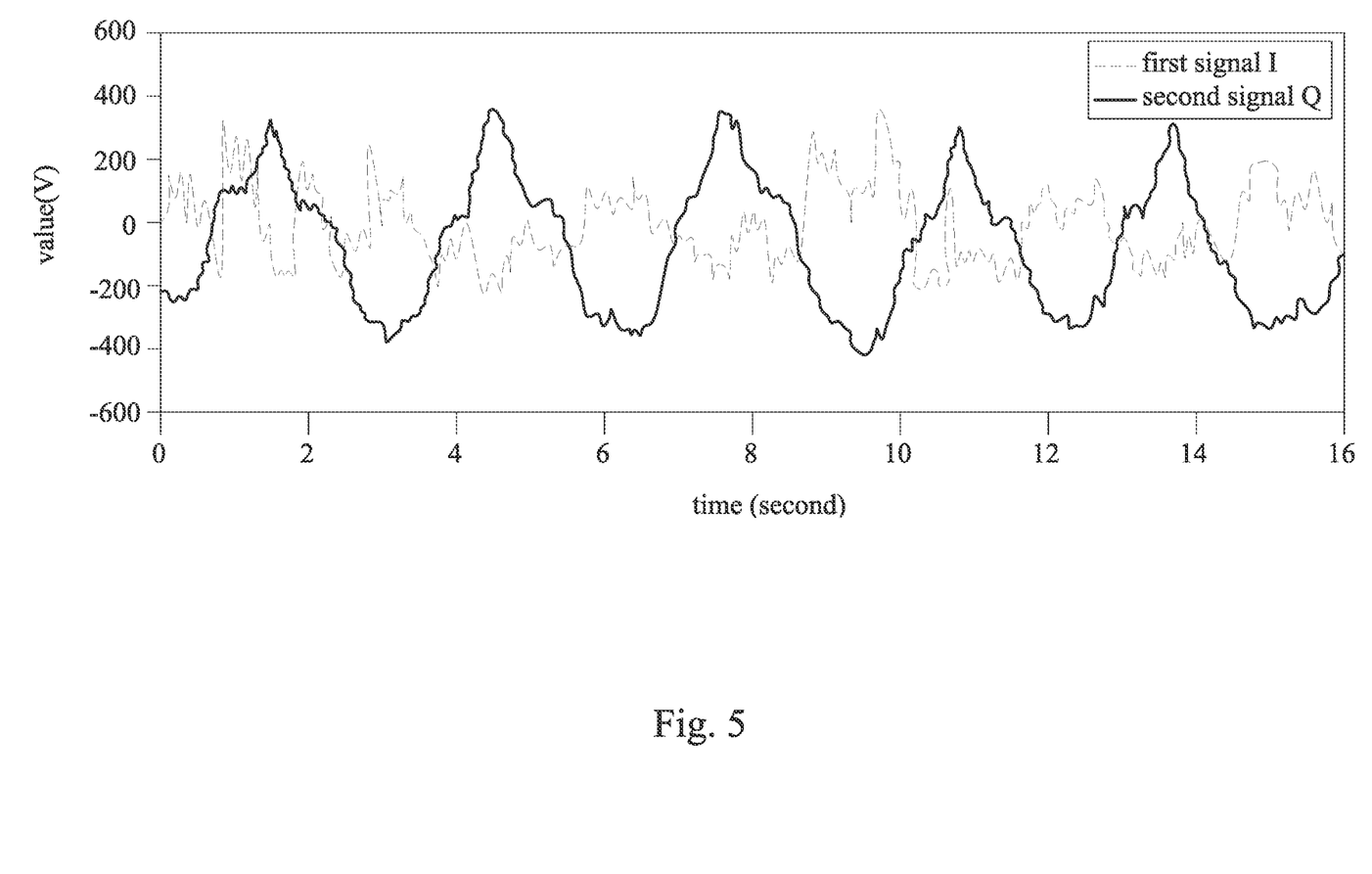
FIG. 5 depicts a schematic diagram of physiological signals measured by a physiological signal measurement device according to some embodiments of the present disclosure.
Figure 6:
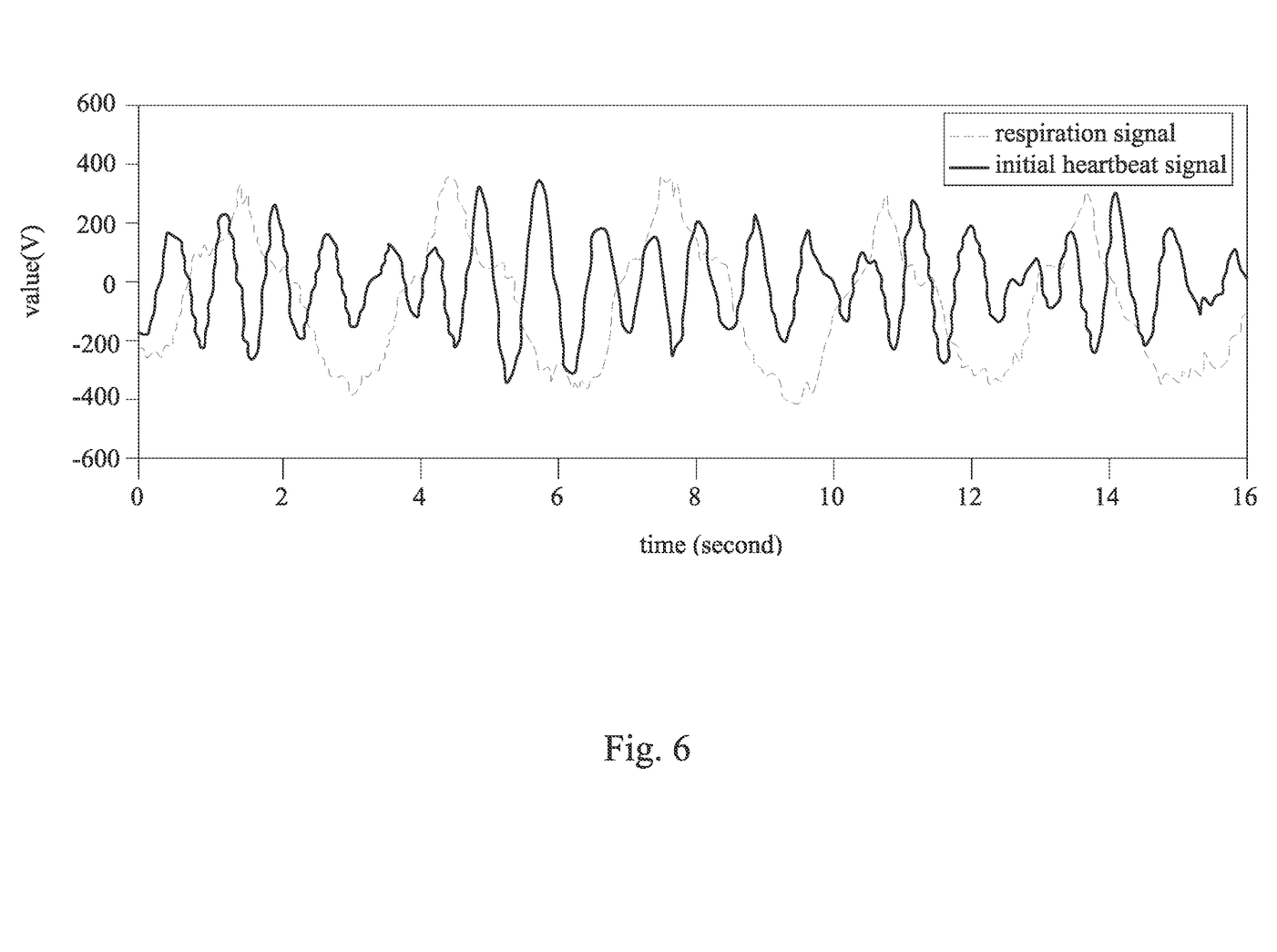
FIG. 6 depicts a schematic diagram of physiological signals analyzed by a physiological signal measurement device according to some embodiments of the present disclosure.
Figure 7:
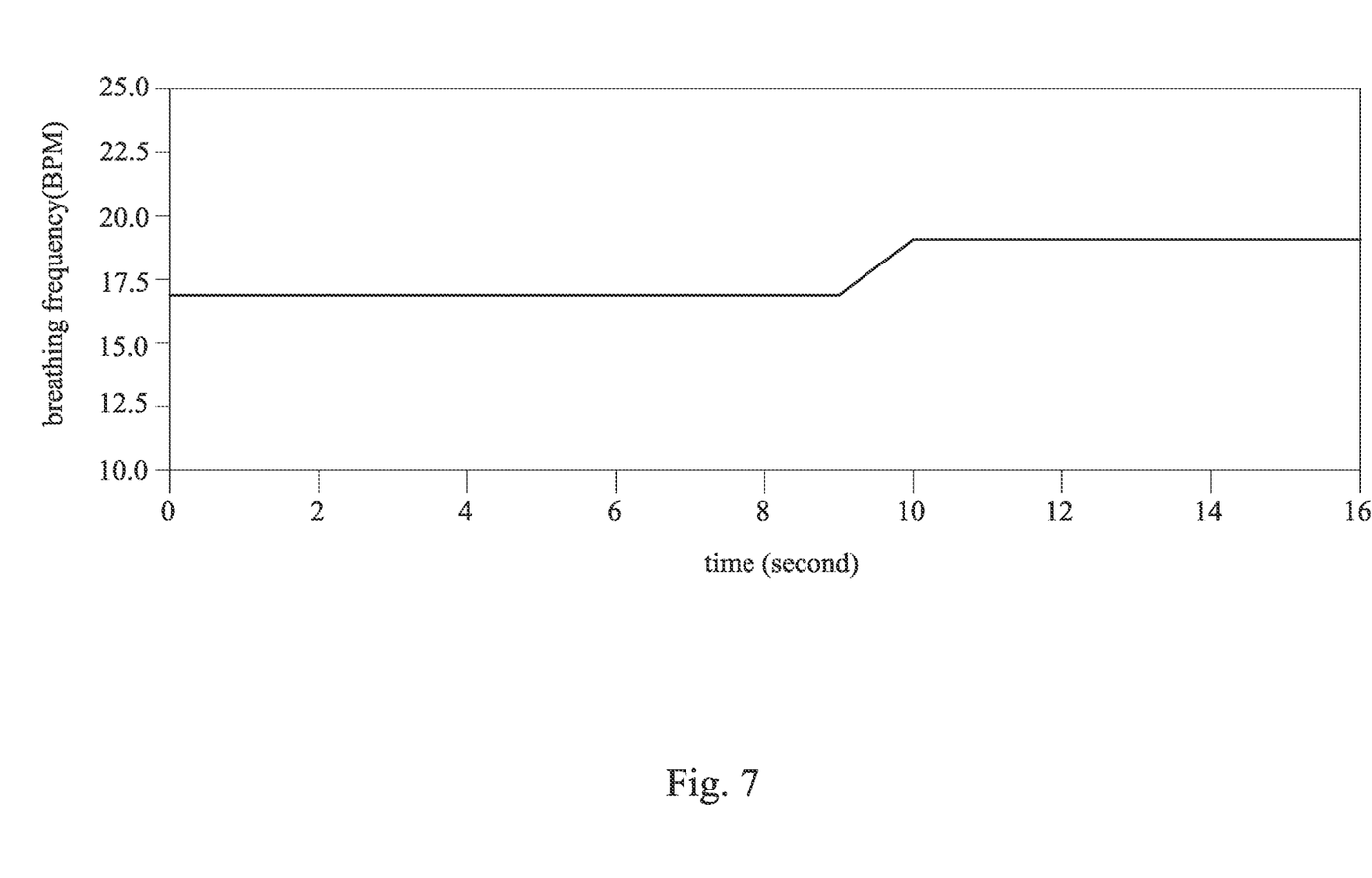
FIG. 7 depicts a schematic diagram of a respiration signal analyzed by a physiological signal measurement device according to some embodiments of the present disclosure.
Figure 8:
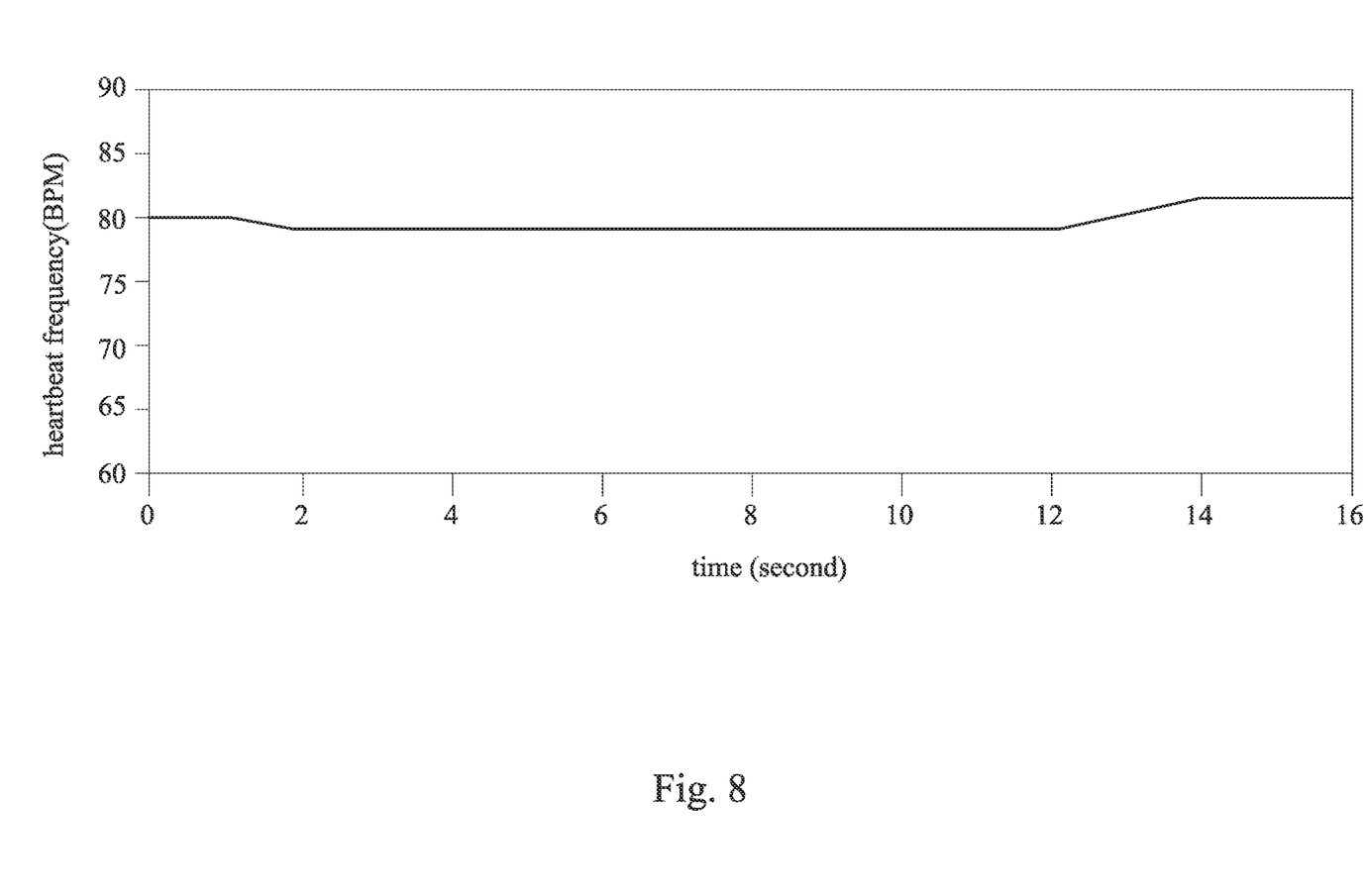
FIG. 8 depicts a schematic diagram of a heartbeat signal analyzed by a physiological signal measurement device according to some embodiments of the present disclosure.

FIG. 4 depicts a flow chart of a method for measuring a physiological signal according to some embodiments of the present disclosure. In some embodiments, the step flow chart of FIG. 4 is a detailed step flow chart of the step 330 of the physiological signal method 300 for measuring a physiological signal 330. In some embodiments, in order to facilitate the understanding of the step 330 of the method 300 for measuring a physiological signal of the present disclosure, please refer to FIG. 5 to FIG. 8 together. FIG. 5 depicts a schematic diagram of physiological signals measured by the physiological signal measurement device 100 according to some embodiments of the present disclosure. FIG. 6 to FIG. 8 depict schematic diagrams of physiological signals analyzed by the physiological signal measurement device 100 according to some embodiments of the present disclosure. Detailed step 331 to step 336 of the step 330 are executed by the processor 120 of the aforementioned physiological signal measurement device 100.

In step 331, a first signal and a second signal are generated according the physiological signal. In some embodiments, please refer to FIG. 1, FIG. 4, and FIG. 5, the radar sensor 110 is configured to generate a first signal I and a second signal Q of different data channels shown in FIG. 5 according to the physiological signal PS1. A phase difference is formed between the first signal I and the second signal Q.

In step 332, one of the first signal and the second signal is selected to generate a plurality of original signals. In some embodiments, please refer to FIG. 1, FIG. 4, and FIG. 5, the processor 120 is configured to select one of the first signal I and the second signal Q. In some embodiments, the processor 120 is configured to select a better signal (e.g. the first signal I) between the first signal I and the second signal Q according to signal conditions of the first signal I and the second signal Q.

In step 333, a first signal processing is performed on the plurality of original signals. In some embodiments, please refer to FIG. 1, FIG. 4 to FIG. 6, following aforementioned step, after the processor 120 is configured to select a better signal (e.g. the first signal I) between the first signal I and the second signal Q shown in FIG. 5, the processor 120 is configured to select better signal (e.g. the first signal I) to generate the plurality of original signals shown in FIG. 6. It should be note that selecting the better signal (e.g. the first signal I) needs to be adjusted by a DC offset method before obtaining the plurality of original signals shown in FIG. 6. A respiration signal and an initial heartbeat signal of the target O can be separated after the plurality of original signals are subjected to the DC offset method. It should be note that a DC signal in the physiological signal PS1 may affect the physiological signal PS1 itself, so the DC signal is selected to be removed from the physiological signal PS1.

In step 334, a respiration signal is captured. In some embodiments, please refer to FIG. 1, FIG. 4, FIG. 6, and FIG. 7, the respiration signal of the target O can be obtained after the plurality of original signals are subjected to the DC offset method. The processor 120 is configured to convert the respiration signal into a periodic variation trend graph of several times per minute shown in FIG. 7. It should be noted that a vertical axis of the periodic variation trend graph is a breathing frequency, and a unit of the breathing frequency is the beats per minute (BPM). A horizontal axis is time, and a unit of the time is second.

In step 335, an initial heartbeat signal is captured, and a second signal processing is performed on the initial heartbeat signal. In some embodiments, please refer FIG. 1, FIG. 4, and FIG. 6, the initial heartbeat signal of target O can be obtained after the plurality of original signals are subjected to the DC offset method. At this time, the processor 120 is configured to perform a second signal processing on the initial heartbeat signal. It should be noted that although a frequency of the heartbeat signal is higher than a frequency of the respiration signal, an amplitude of the heartbeat signal is usually lower than an amplitude of the respiration signal. Therefore, the heartbeat signal needs to undergo multiple signal processing.

In some embodiments, the processor 120 is configured to perform high-pass filtering and moving sun on the initial heartbeat signal to obtain the heartbeat signal. It should be noted that the present disclosure discloses that the second signal processing is performed on the initial heartbeat signal by high-pass filtering and moving sun, but not limited to embodiments of the present disclosure in practice.

In step 336, a heartbeat signal is captured. In some embodiments, please refer to FIG. 1, FIG. 4, FIG. 6, and FIG. 8, after the processor 120 is configured to perform the second signal processing on the initial heartbeat signal shown in FIG. 6, the heartbeat signal shown in FIG. 8 is obtained. The processor 120 is configured to convert the heartbeat signal into a periodic variation trend graph of several times per minute shown in FIG. 8. It should be noted that a vertical axis of the periodic variation trend graph of the heartbeat signal shown in FIG. 8 is a heartbeat frequency, and a unit of the heartbeat frequency is beats per minute BPM). A horizontal axis is time, and a unit of the time is second.

In some embodiments, a signal analysis method of the aforementioned respiration signal and the heartbeat signal includes time domain analysis.

In some embodiments, please refer to FIG. 1, FIG. 5 to FIG. 8, the processor 120 is further configured to transmit signal diagrams of FIG. 5 to FIG. 8 to a display panel of an electronic device 900 for a user to interact with the GUI of the display panel.

Based on the above embodiments, the present disclosure provides a method 300 for measuring a physiological signal and a physiological signal measurement device 100. A design of a physiological signal measurement device 100 of the present disclosure can measure a physiological signal of a target O by a non-contact measurement. A sensing signal of a physiological signal measurement device 100 is high frequency signal, and is not affected by a light source. Since a method 300 for measuring a physiological signal of the present disclosure does not measure a face or an image information of a target. Therefore, a method 300 for measuring a physiological signal and a physiological signal measurement device 100 of the present disclosure do not involve legal issues of privacy information.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. A method for measuring a physiological signal, comprising:
   detecting a first physiological signal of a target;
   wherein detecting the first physiological signal of the target comprises:
      determining whether the first physiological signal of the target is sensed; and
      adjusting a beam direction of a sensing signal of a plurality of beam-steerable liquid crystal antenna components of a radar sensor if the first physiological signal of the target is not sensed;
   receiving the first physiological signal to generate a first signal and a second signal by the radar sensor;
   selecting one of the first signal and the second signal to generate a plurality of original signals, wherein a phase difference is formed between the first signal and the second signal; and
   capturing a respiration signal and a heartbeat signal according to the plurality of original signals.

2. The method for measuring the physiological signal of claim 1, wherein the target comprises a first target and a second target, wherein the adjusting the beam direction of the sensing signal of the plurality of beam-steerable liquid crystal antenna components of the radar sensor comprises:
   adjusting the sensing signal to emit along a first beam direction so as to detect the first physiological signal of the first target;
   adjusting the sensing signal to emit along a second beam direction so as to detect a second physiological signal of the second target; and
   adjusting the sensing signal to emit along a third beam direction if the first target and the second target are not sensed, wherein the first beam direction, the second beam direction, and the third beam direction are not parallel to each other.

3. The method for measuring the physiological signal of claim 2, further comprising:
   recording the first physiological signal of the first target to analyze if the first target is sensed, and
   adjusting the sensing signal to emit along the second beam direction so as to detect the second physiological signal of the second target.

4. The method for measuring the physiological signal of claim 2, wherein each of the first target and the second target is in a stationary state.

5. The method for measuring the physiological signal of claim 1, wherein selecting one of the first signal and the second signal to generate the plurality of original signals comprises:
adjusting the plurality of original signals by a DC offset method.

6. The method for measuring the physiological signal of claim 5, wherein capturing the respiration signal and the heartbeat signal according to the plurality of original signals comprise:
performing a first signal processing on the plurality of original signals so as to obtain an initial heartbeat signal corresponding to the heartbeat signal and the respiration signal; and
performing a second signal processing on the initial heartbeat signal so as to obtain the heartbeat signal.

7. The method for measuring the physiological signal of claim 1, wherein the radar sensor comprises a wireless high frequency circuit, wherein the wireless high frequency circuit comprises the plurality of beam-steerable liquid crystal antenna components.

8. The method for measuring the physiological signal of claim 1, further comprising:
outputting the heartbeat signal and the respiration signal to a graphical user interface of a display panel of an electronic device.

9. The method for measuring the physiological signal of claim 8, wherein the electronic device comprises one of mobile phones, computers, notebook computers and wearable devices.

10. A physiological signal measurement device, comprising:
a radar sensor, configured to emit a sensing signal so as to detect a physiological signal of a target, and configured to generate a first signal and a second signal according to the physiological signal, wherein the radar sensor is further configured to determine whether the physiological signal of the target is sensed, wherein the radar sensor is further configured to adjust a beam direction of the sensing signal of a plurality of beam-steerable liquid crystal antenna components of the radar sensor if the physiological signal of the target is not sensed; and
a processor, coupled to the radar sensor, wherein the processor is configured to selecting one of the first signal and the second signal to generate a plurality of original signals, wherein a phase difference is formed between the first signal and the second signal, wherein the processor is configured to capture a respiration signal and a heartbeat signal according to the plurality of original signals.

11. The physiological signal measurement device of claim 10, wherein the radar sensor comprises a wireless high frequency circuit, wherein the wireless high frequency circuit comprises the plurality of beam-steerable liquid crystal antenna components, wherein each of the plurality of beam-steerable liquid crystal antenna components is configured to emit the sensing signal so as to receive the physiological signal of the target.

12. The physiological signal measurement device of claim 11, wherein the plurality of beam-steerable liquid crystal antenna components are arranged as an array.

13. The physiological signal measurement device of claim 10, further comprising:
an amplifier circuit, coupled to the radar sensor and the processor, wherein the amplifier circuit is configured to transmit the first signal and the second signal of the radar sensor and is configured to increase a plurality of output powers of the first signal and the second signal.

14. The physiological signal measurement device of claim 10,
wherein the processor is further configured to output the heartbeat signal and the respiration signal to a graphical user interface of a display panel of an electronic device.

15. The physiological signal measurement device of claim 14, wherein the electronic device comprises one of mobile phones, computers, notebook computers and wearable devices.

16. The physiological signal measurement device of claim 10, further comprising:
a reference signal source, configured to generate a reference signal or a plurality of reference signal.

17. The physiological signal measurement device of claim 16, further comprising:
a frequency synthesizer, coupled to the reference signal source and the radar sensor, wherein the frequency synthesizer is configured to generate a plurality of discrete frequency signals according to the reference signal or the plurality of reference signal.

18. The physiological signal measurement device of claim 17, further comprising:
a loop filter, coupled to the frequency synthesizer and the radar sensor, wherein the loop filter is configured to remove a disturbed high frequency signal in the physiological signal.

19. The physiological signal measurement device of claim 10, wherein the first signal and the second signal are signals of different data channels.

* * * * *